(12) United States Patent
Ewers et al.

(10) Patent No.: US 8,512,362 B2
(45) Date of Patent: Aug. 20, 2013

(54) ENDOSCOPIC LIGATION

(75) Inventors: Richard C. Ewers, Fullerton, CA (US); Christopher James Earley, San Clemente, CA (US); Barton P. Bandy, Orange, CA (US); Eugene G. Chen, Carlsbad, CA (US); Haio Fauser, Encinitas, CA (US)

(73) Assignee: USGI Medical Inc., San Clemente, CA (US)

( * ) Notice: Subject to any disclaimer, the term of this patent is extended or adjusted under 35 U.S.C. 154(b) by 829 days.

(21) Appl. No.: 12/265,672

(22) Filed: Nov. 5, 2008

(65) Prior Publication Data

US 2009/0125038 A1 May 14, 2009

Related U.S. Application Data

(60) Provisional application No. 60/985,473, filed on Nov. 5, 2007.

(51) Int. Cl.
*A61B 17/128* (2006.01)

(52) U.S. Cl.
USPC ........... 606/158; 606/139; 606/142; 606/157; 606/151

(58) Field of Classification Search
USPC ................. 606/139, 148, 142–144, 157–158, 606/151, 1, 205; 600/37; 128/898
See application file for complete search history.

(56) References Cited

U.S. PATENT DOCUMENTS

| | | | | |
|---|---|---|---|---|
| 3,735,762 A * | 5/1973 | Bryan et al. | ................... | 606/143 |
| 4,708,140 A * | 11/1987 | Baron | ........................... | 606/158 |
| 5,074,869 A * | 12/1991 | Daicoff | .......................... | 606/158 |
| 5,100,418 A * | 3/1992 | Yoon et al. | .................... | 606/139 |
| 5,312,423 A * | 5/1994 | Rosenbluth et al. | .......... | 606/148 |
| 5,411,481 A * | 5/1995 | Allen et al. | .................... | 606/144 |
| 5,609,599 A * | 3/1997 | Levin | ............................ | 606/153 |
| 5,700,272 A * | 12/1997 | Gordon et al. | ................ | 606/144 |
| 5,810,845 A * | 9/1998 | Yoon | ............................. | 606/139 |
| 5,810,847 A * | 9/1998 | Laufer et al. | ................... | 606/142 |
| 5,897,562 A * | 4/1999 | Bolanos et al. | ............... | 606/139 |
| 6,648,898 B1 * | 11/2003 | Baxter | .......................... | 606/142 |
| 6,830,546 B1 * | 12/2004 | Chin et al. | .................... | 600/206 |
| 7,462,188 B2 * | 12/2008 | McIntosh | ..................... | 606/213 |
| 7,569,062 B1 * | 8/2009 | Kuehn et al. | ................... | 606/139 |
| 7,753,841 B2 * | 7/2010 | Jarsaillon et al. | ............... | 600/37 |
| 7,918,845 B2 * | 4/2011 | Saadat et al. | ..................... | 606/1 |
| 7,972,265 B1 * | 7/2011 | Chin et al. | .................... | 600/206 |
| 8,133,242 B1 * | 3/2012 | Quinn et al. | ................... | 606/157 |
| 2004/0122448 A1 * | 6/2004 | Levine | ........................... | 606/139 |
| 2004/0162567 A9 * | 8/2004 | Adams | .......................... | 606/139 |
| 2005/0149063 A1 * | 7/2005 | Young et al. | ................... | 606/142 |
| 2006/0237023 A1 * | 10/2006 | Cox et al. | ....................... | 128/898 |
| 2006/0264987 A1 * | 11/2006 | Sgro | .............................. | 606/157 |
| 2007/0175488 A1 * | 8/2007 | Cox et al. | ....................... | 128/898 |
| 2007/0185374 A1 * | 8/2007 | Kick et al. | ...................... | 600/37 |
| 2008/0300608 A1 * | 12/2008 | Measamer | ..................... | 606/139 |

(Continued)

*Primary Examiner* — Corrine M McDermott
*Assistant Examiner* — Mark Mashack
(74) *Attorney, Agent, or Firm* — Kenneth H. Ohriner; Perkins Coie LLP

(57) ABSTRACT

A ligature delivery device includes a control member, an elongated shaft, and an end effector attached to the distal end of the elongated shaft. An activation mechanism provides an user-operable connection between the control member and the end effector. In several embodiments, the end effector includes a reverse grasping mechanism. Several embodiments of ligature devices are adapted to be deployed endoscopically and/or translumenally using the reverse-grasping delivery device.

16 Claims, 13 Drawing Sheets

(56) References Cited

U.S. PATENT DOCUMENTS

2008/0312652 A1* 12/2008 Bell et al. .................... 606/48
2008/0319435 A1* 12/2008 Rioux et al. .................. 606/33
2009/0209986 A1* 8/2009 Stewart et al. ............... 606/157
2010/0145361 A1* 6/2010 Francischelli et al. ....... 606/139

* cited by examiner

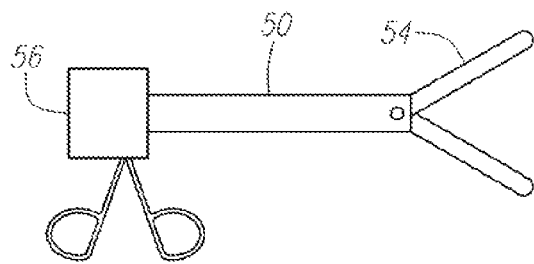
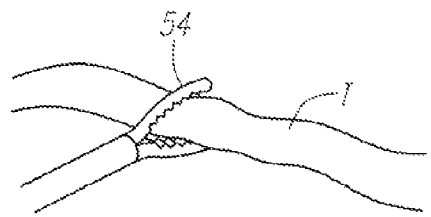
FIG. 1A  FIG. 1B
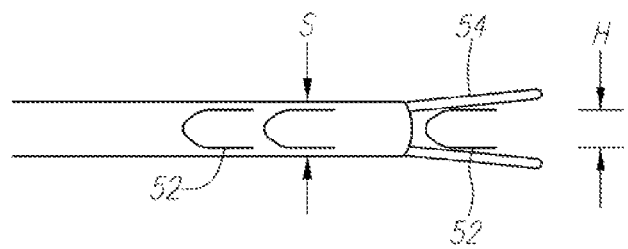
FIG. 2
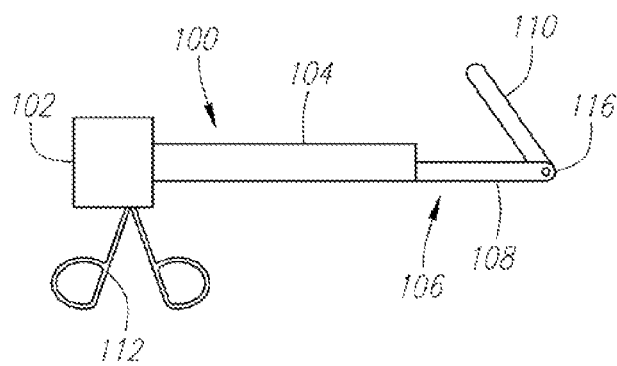
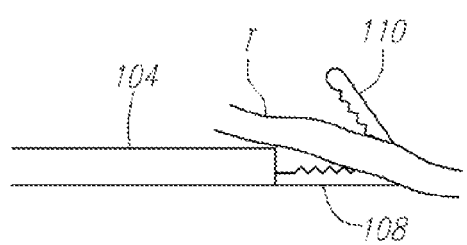
FIG. 3A  FIG. 3B
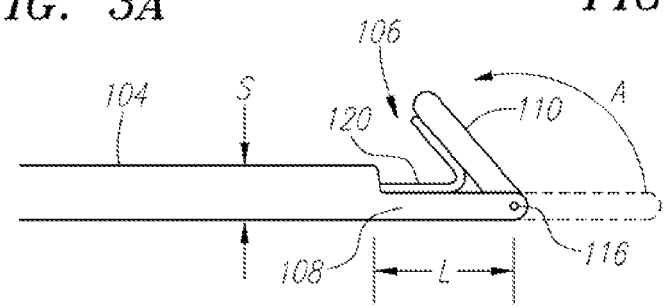
FIG. 4

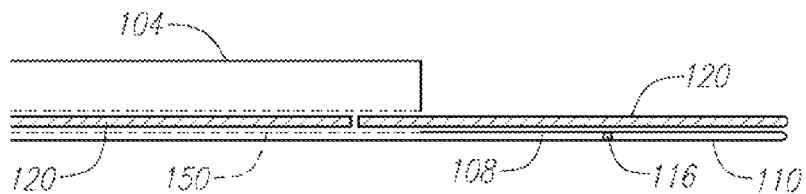
FIG. 8A
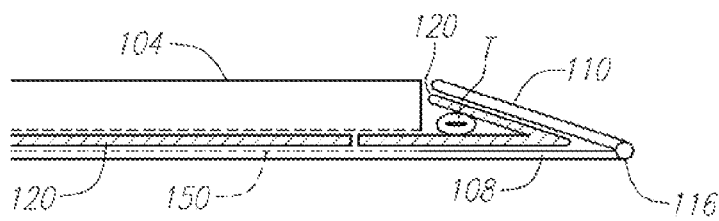
FIG. 8B
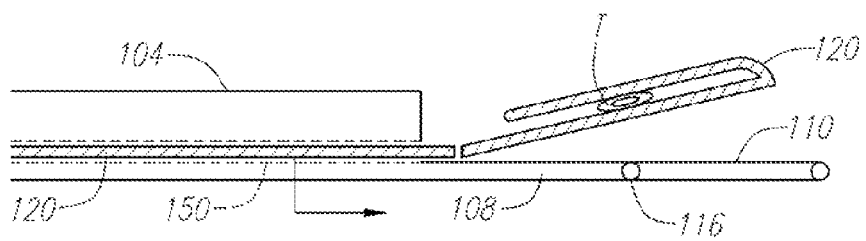
FIG. 8C
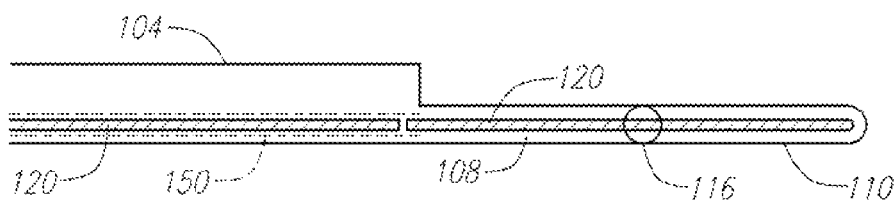
FIG. 9A
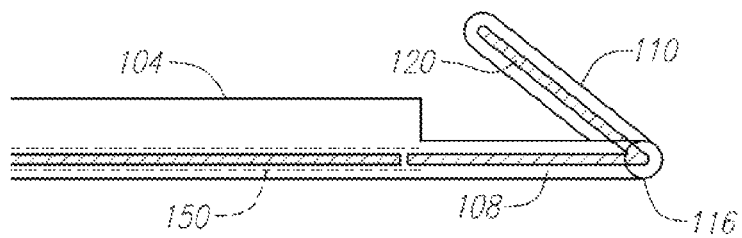
FIG. 9B
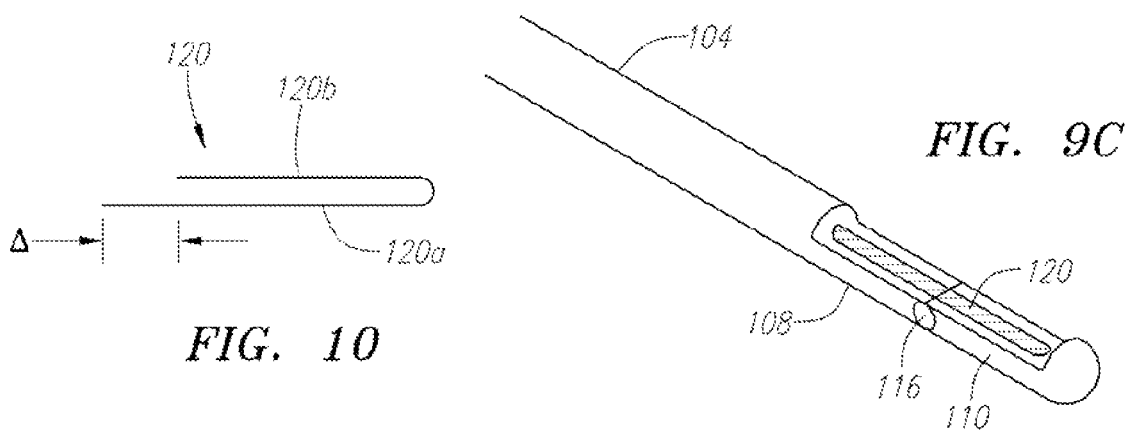
FIG. 10
FIG. 9C

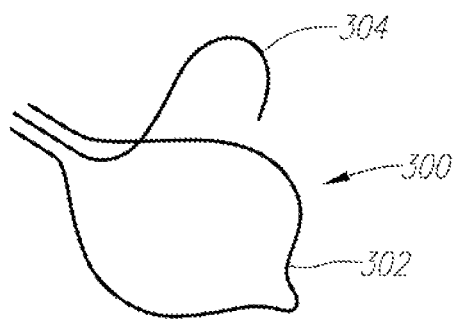
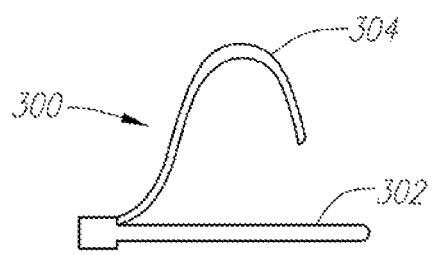
*FIG. 20A*   *FIG. 20B*
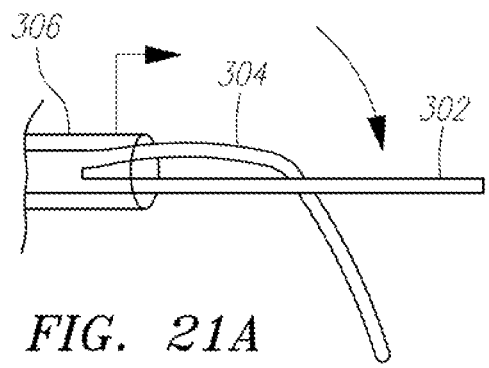
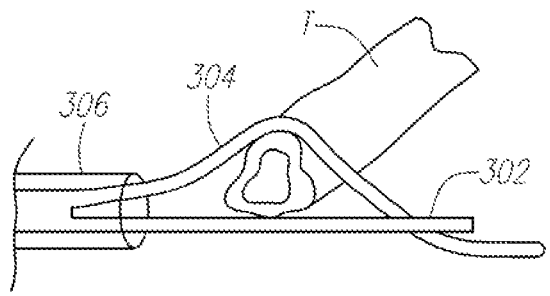
*FIG. 21A*   *FIG. 21B*
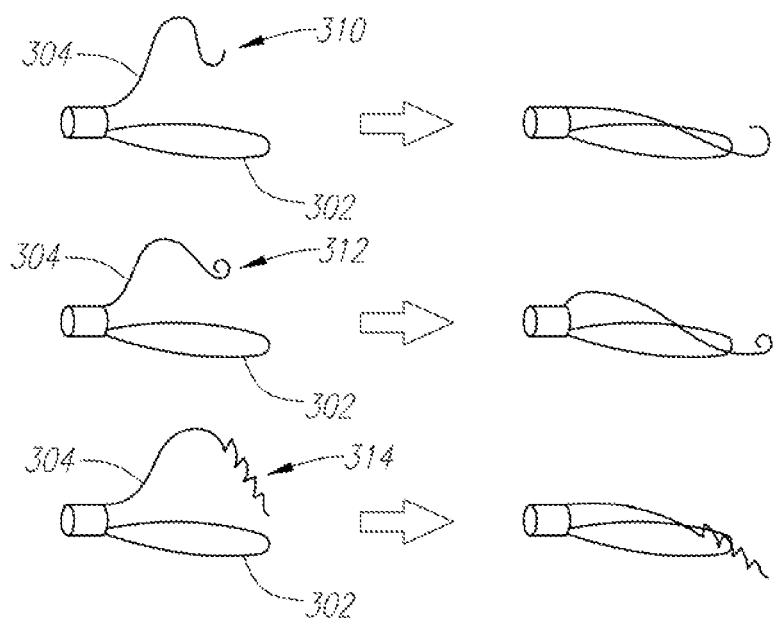
*FIG. 22*

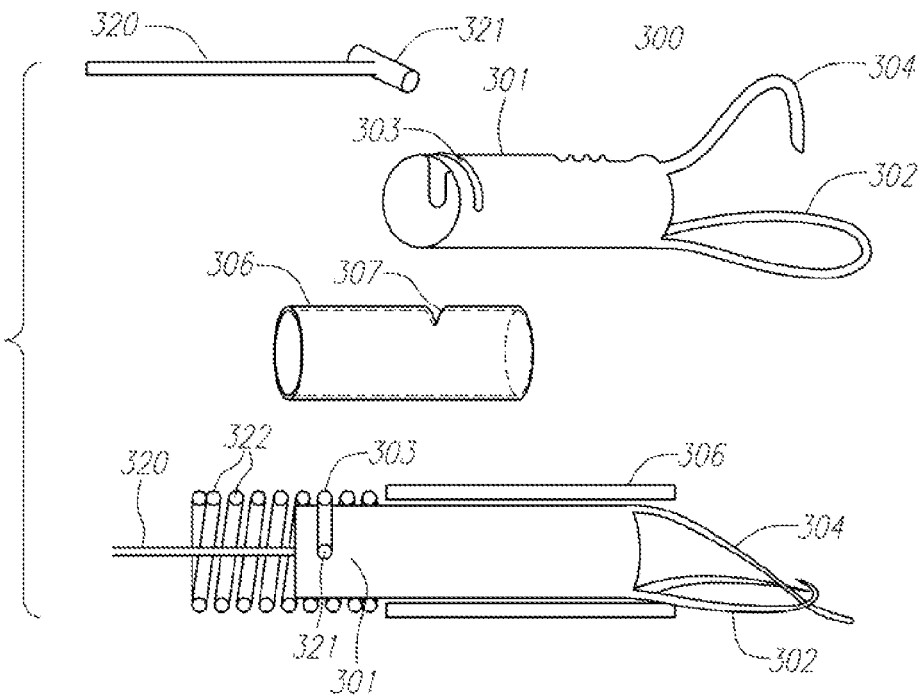
FIG. 23
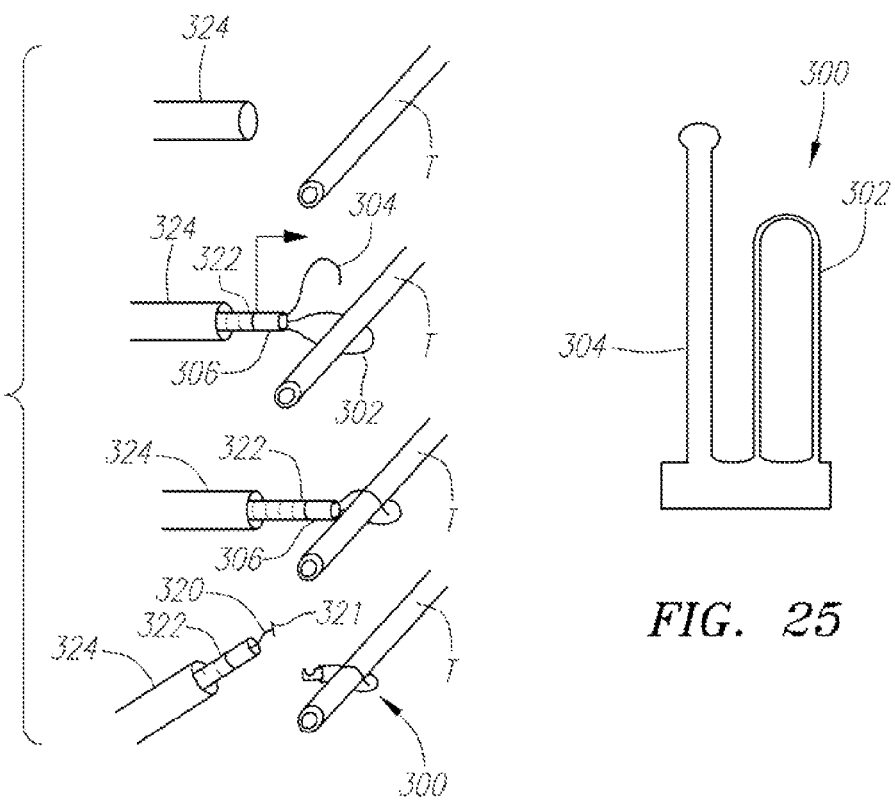
FIG. 24
FIG. 25

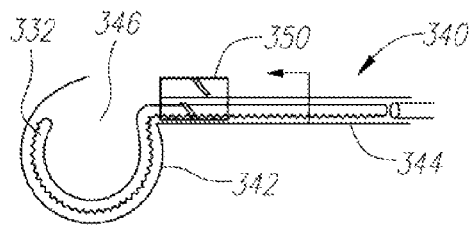
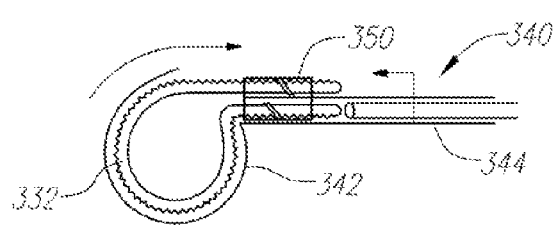
FIG. 26A        FIG. 26B
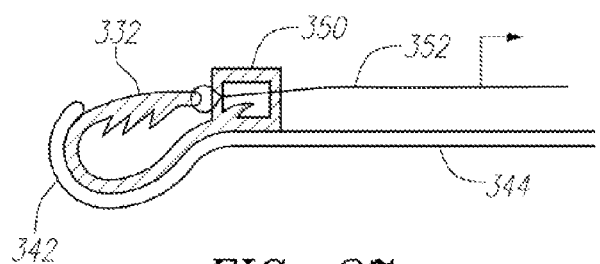
FIG. 27
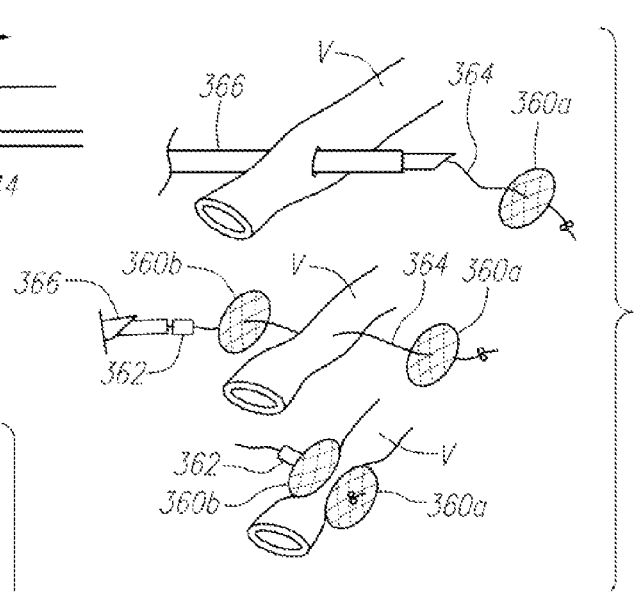
FIG. 28
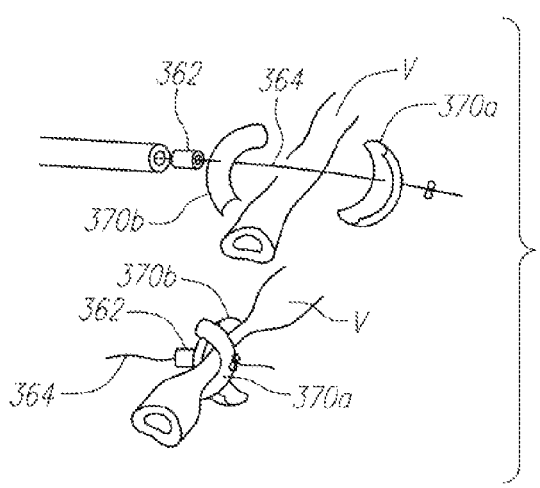
FIG. 29
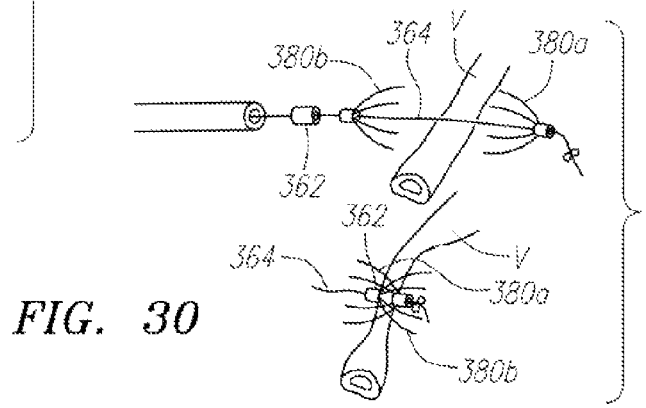
FIG. 30

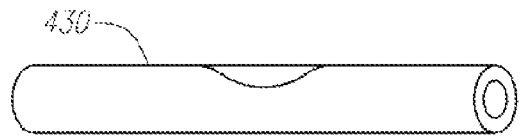
FIG. 38A
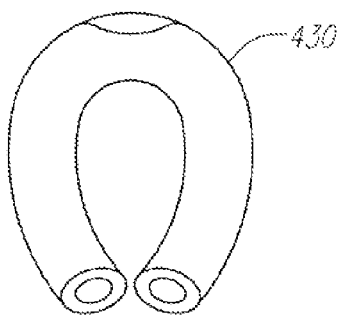
FIG. 38B
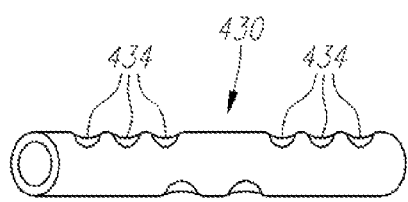
FIG. 39
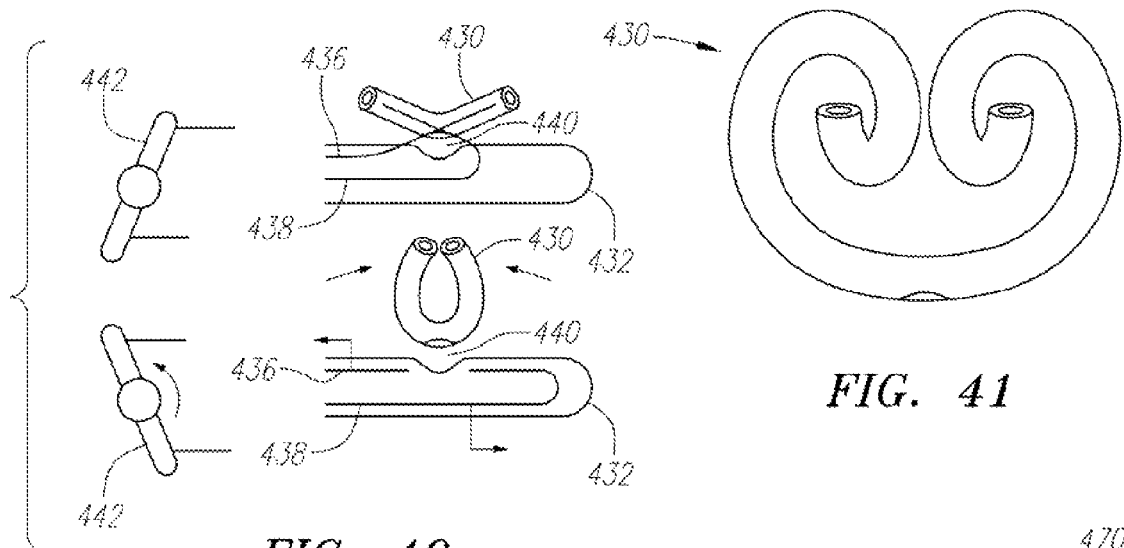
FIG. 40
FIG. 41
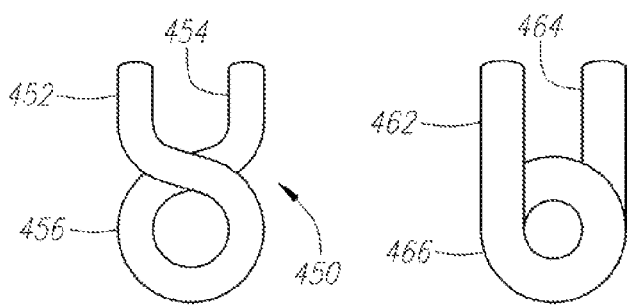
FIG. 42   FIG. 43
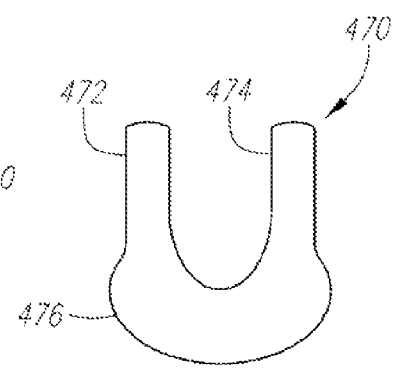
FIG. 44

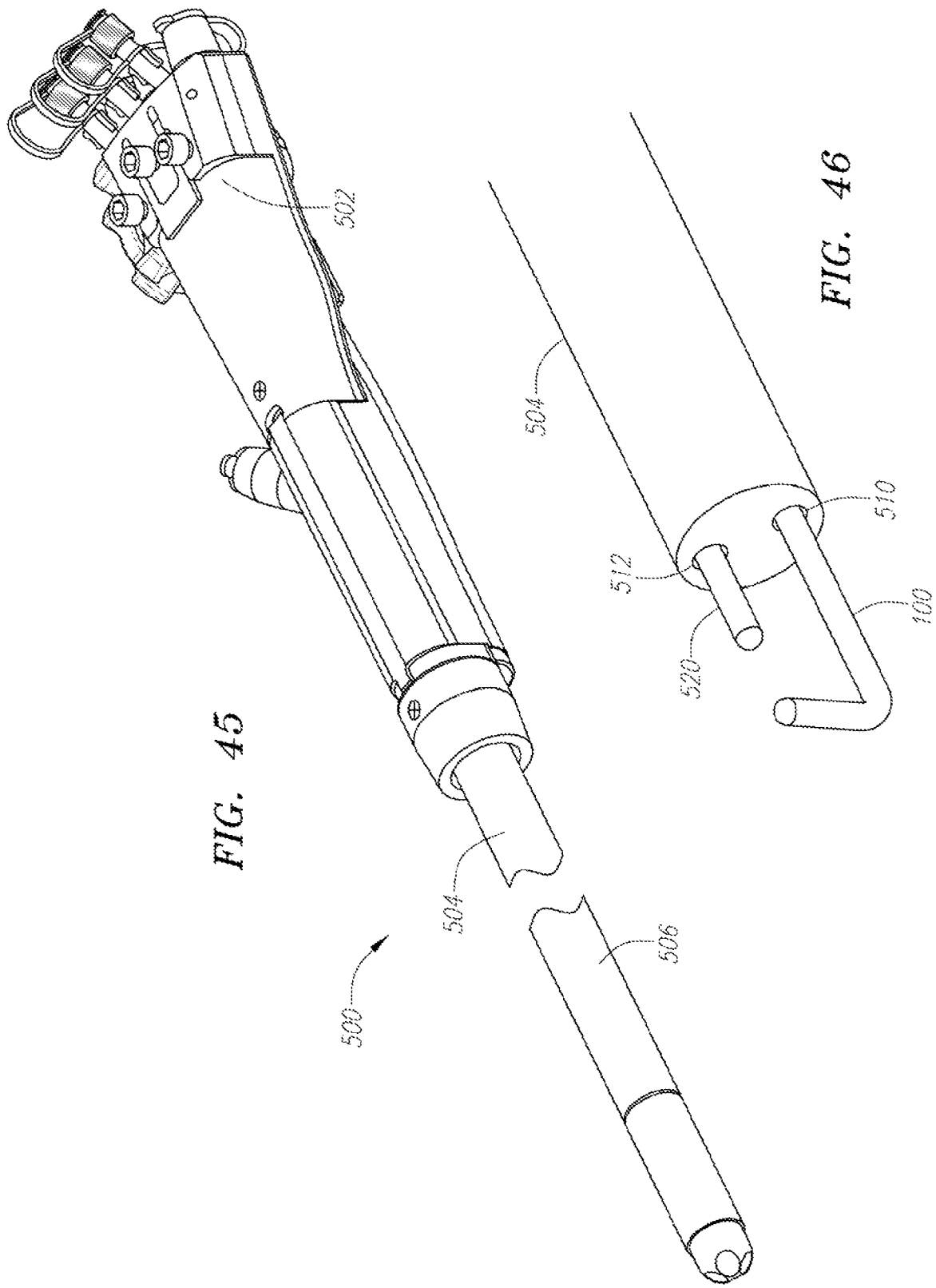

ENDOSCOPIC LIGATION

RELATED APPLICATION DATA

This application claims priority to and the benefit of the filing date of U.S. Provisional Patent Application Ser. No. 60/985,473, filed Nov. 5, 2007. The foregoing application is hereby incorporated by reference in its entirety.

FIELD OF THE INVENTION

The present invention relates to surgical instruments used to engage, manipulate, and ligate tissue, and methods of their use.

BACKGROUND OF THE INVENTION

The present disclosure pertains to devices and methods for endoscopically ligating natural or artificial structures. Ligation is the act of making a ligature (tie). In medicine, a ligature is a device, similar to a tourniquet, usually of thread or string, tied around a limb, blood vessel or similar structure to restrict blood flow. For example, a ligature can be used for tumor strangulation, carried out before removal. A ligature can also be defined as a constricting or compressing device used to control venous and arterial circulation to an extremity for a period of time. Pressure is applied circumferentially upon the skin and underlying tissues of a limb; this pressure is transferred to the walls of vessels, causing them to become temporarily occluded. In surgery, the term "ligate" has come to mean the tying off or constriction of vessels, ducts or other tissue to prevent bleeding or leaking.

In open surgery and in extracorporeal applications a ligature can be easily constructed and applied. For example a surgeon's hands can manipulate a suture length onto and around a vessel or limb. This suture length can then be tied to constrict and fixed in place with a knot.

In laparoscopy, one common way to ligate tissue is to use multiple laparoscopic graspers in conjunction with suture. This technique consists of an opposing jaw grasping tip mounted on an elongated rigid shaft with proximal control handles. One or more of these are used through access points at positions relative to each other to allow complementary interaction. The instruments are used analogous to multiple hands to acquire, position, and tie suture in the form of a constricting knotted assembly. This is a skill intensive method that can be particularly challenging in the hands of a less experienced practitioner or in locations where access and/or visualization is difficult.

Alternatively, the ligation is augmented or simplified by eliminating the laparoscopic knot tying step, in place of which the knot is tied extracorporeally and slid into position. A knot delivery device that is used for these types of laparoscopic procedures is the Quik-Stitch™ endoscopic suturing system offered by Pare Surgical, Inc. Another simplification is using a clip or knot replacement device.

A widely utilized form of ligature in surgery, both open or laparoscopic, is a clip. Most conventional clips consist of a piece of metal wire or strip formed into a "V" or "U" shape. These are loaded into activatable/closable jaws of a clip delivery device, such as the device 50 illustrated in FIGS. 1A-B and 2. In the open state the clip 52 and delivery jaws 54 are positioned onto the tissue T to be ligated. The device is positioned in such a way so that the arms of the clip 52 are on either side of the target site. The jaws 54 are then closed under control of an actuation device associated with the device handle 56. This squeezes both clip 52 and tissue T into a pinched off configuration. The clip 52 is permanently deformed in the pinched configuration thus maintaining the ligature. Multiple clips are often used. Often the delivery jaws 54 are configured at a slight angle to the longitudinal axis of the instrument shaft to aid in visualization and positioning. This type of device is available in single fire/reloadable instruments and multi-fire instruments.

Clips and clip applier devices have a number of limitations. First, there are limitations on clip size. Because the clips are pre-shaped open they can be no wider than the size of the entry port/trocar minus the room necessary for the jaws of the delivery device. For example, a 10 mm trocar compatible clip applier may have jaws that require 2 mm of thickness, thus reducing the potential opening space "H" of the clip to 8 mm. It would be desirable to have a clip that is capable of expanding wider than the shaft size "S" of the delivery tool.

Second, the clip needs to be permanently deformed so the delivery tool must be able to deliver sufficient closing force. This becomes increasingly challenging for an elongated, flexible delivery device.

Third, the clip does not actually encircle the material to be ligated. Therefore, there is a potential for the clip to slip along the vessel or to be dislodged completely, lessening or eliminating the ligating effect.

More recently, devices have been constructed that address some of the limitations of the conventional ligation clips. One example of such a device is the Hem-o-lok™ ligation system offered by Teleflex Medical. The Hem-o-lok™ device is a hinged plastic clip that snaps closed to form a closed path compressed loop. In endoscopic applications it is more difficult to gain the exposure and maneuverability necessary to apply a suture or clip. Also, it is more difficult to handle the suture precisely for proper tensioning and knotting using endoscopic instruments. This is difficult enough in laparoscopy where the instruments are rigid and can be used at alternate engagement angles from the various trocar sites. The difficulty increases even more in endoscopic environments where the instruments are long, flexible, and may be working through lengthy, tortuous pathways

SUMMARY

In one general aspect, a medical instrument according to the present invention includes a ligature and a ligature delivery device. The ligature and delivery device are adapted for use during open surgery, laparoscopic surgery, endoscopic surgery, or translumenal surgery. In several preferred embodiments, the delivery device includes a handle, a shaft having a flexible portion, and an end effector adapted to deploy the ligature. The end effector and flexible shaft have a small cross-sectional profile such that the delivery device is able to pass through a small diameter lumen to be routed to a site within a patient's body. In several other preferred embodiments, the delivery device has an elongated, flexible shaft that allows the instrument to be passed through tortuous anatomy, either as a standalone instrument or as an instrument to be passed through a lumen of an overtube. The end effector may be used to engage, grasp, acquire, position, or otherwise manipulate tissue (e.g., an organ, vessel, or other tissue) within a patient. The delivery device is suitable for use as a standalone instrument, or it may be used in combination with other instruments that provide independent or related functions.

In several embodiments, the end effector of the delivery device includes a movable arm or jaw that moves (e.g., rotates) proximally (i.e., toward the handle) upon actuation by the user. For example, in an embodiment, the movable arm rotates around a distal pivot such that the distal-most portion of the arm moves through an arc of substantially 180 degrees to abut the distal end of the flexible shaft. This "reverse" grasping motion provides several advantages over conventional forward-directed clip applying delivery devices.

In a second general aspect, a method for applying a ligature to a target site (e.g., tissue, organ, vessel, or other substrate) includes the steps of providing a delivery device having a ligature at a location adjacent to a tissue site, moving an end effector of the delivery device to a position distal of the target site, actuating a movable arm of the delivery device to an open position defining a proximally-oriented opening, moving the end effector proximally to engage the target site, and deploying the ligature with the end effector. In several embodiments, the method is performed using a delivery device that is placed near the target site either endoscopically, laparoscopically, translumenally, or during open surgery. In an embodiment, the delivery device is advanced to a tissue site via a natural body orifice.

In a third general aspect, several embodiments of ligature devices that are adapted to ligate a target site (e.g., tissue, organ, vessel, or other substrate) are provided. In several embodiments, the ligature devices have a low profile delivery state and a relatively high profile deployment state, are capable of encircling the target site, and are able to be configured into a secure constricting form. In some embodiments, the ligature is deployed using a delivery device having a distal end effector, a shaft, a handle, and an actuation control associated with the handle and coupled to the end effector. The delivery device has a length in the range of 20 to 200 cm. The shaft is rigid or flexible. In some embodiments, the shaft includes both flexible and semi-flexible/rigid sections wherein the distal length and majority of the shaft is flexible and terminates with a relatively rigid section near the actuation control. This structure provides the delivery device with the capability to navigate tortuous anatomies or lumens while providing the user with a stable proximal end. In some embodiments, the ligature has a crossing profile of 2-10 mm in its low profile state. In some embodiments, the end effector is expandable to allow for encirclement of a 15 mm structure. The ligature and end effector have the capability to constrict down to 75%-0% of the ligature application size (partial constriction to full constriction). The applied ligature is detachable from the shaft and actuator. The actuator and shaft are reloadable multiple times and the device is capable of pre-loaded multi-firings.

In a fourth general aspect, ligation systems are provided. The ligation systems include a ligature, a ligature delivery device, and an endoscopic or translumenal access device.

BRIEF DESCRIPTION OF THE DRAWINGS

FIGS. 1A and 1B are schematic diagrams of a prior art clip applier.

FIG. 2 is a schematic diagram of a distal end of the clip applier of FIGS. 1A-B.

FIGS. 3A-B are schematic diagrams of a reverse grasping ligature delivery device in accordance with the present invention.

FIG. 4 is a schematic diagram of a distal end of the reverse grasping ligature delivery device of FIGS. 3A-B.

FIGS. 8A-C are side cross-sectional views of an embodiment of an end effector of a reverse grasping ligature delivery device.

FIGS. 9A-C are side cross-sectional views of another embodiment of an end effector of a reverse grasping ligature delivery device.

FIG. 10 is a side view of an embodiment of a ligature device.

FIGS. 20A-B are perspective and side views, respectively, of an embodiment of a finger snare type ligature device.

FIGS. 21A-B are side views of a finger snare ligature device in free space and deployed on a portion of tissue, respectively.

FIG. 22 includes perspective views of embodiments of finger snare type ligature devices.

FIG. 23 includes side views of an embodiment of a finger snare type ligature device and a portion of an embodiment of a delivery mechanism.

FIG. 24 shows a deployment of a finger snare type ligature device.

FIG. 25 is a plan view of a flattened pattern for a finger snare type ligature device.

FIGS. 26A-B are side cross-sectional views of an embodiment of a ligature device.

FIG. 27 is a side cross-sectional view of an embodiment of a ligature device.

FIG. 28 shows a deployment of an embodiment of a ligature device.

FIG. 29 shows a deployment of another embodiment of a ligature device.

FIG. 30 shows a deployment of another embodiment of a ligature device.

FIGS. 38A-B and 39 include perspective views of embodiments of ligature devices.

FIG. 40 shows a deployment of an embodiment of a ligature device.

FIG. 41 includes a perspective view of another embodiment of a ligature device.

FIGS. 42-44 include perspective views of embodiments of stored energy type ligature devices.

FIG. 45 is a perspective view of an endoscopic or translumenal access device.

FIG. 46 is an end view of the access device of FIG. 45.

DETAILED DESCRIPTION

Figure 5A:
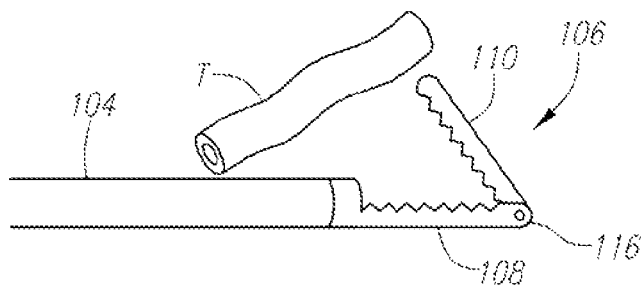
FIGS. 5A-C are side views of a reverse grasping ligature delivery device approaching, acquiring, and manipulating a target tissue.

Endoscopic, laparoscopic, endolumenal, and translumenal diagnostic and surgical methods and devices are described herein. In several embodiments, the methods entail performing procedures by gaining access to the internal organs of a patient through the patient's mouth or other natural orifices, reducing or eliminating the need for external incisions into the body. Operating through the body's natural orifices offers promise for faster healing times, less scarring and less pain which could lead to reduced hospitalization and quicker recovery. In other embodiments, access is gained through an access port, such as a minimally invasive access port, such as a laparoscopic access port.

USGI Medical, Inc. of San Clemente, Calif. has developed several devices and methods that facilitate endoscopic, laparoscopic, endolumenal, and translumenal diagnostic and therapeutic procedures. Several endoscopic access devices are described, for example, in the following United States patent applications:

TABLE 1

| U.S. patent application Ser. No. | Filing Date |
| --- | --- |
| 10/346,709 | Jan. 15, 2003 |
| 10/458,060 | Jun. 9, 2003 |
| 10/797,485 | Mar. 9, 2004 |
| 11/129,513 | May 13, 2005 |
| 11/365,088 | Feb. 28, 2006 |
| 11/738,297 | Apr. 20, 2007 |
| 11/750,986 | May 18, 2007 |
| 12/061,591 | Apr. 2, 2008 |

Several tissue manipulation and tissue anchor delivery devices are described in the following United States patent applications:

TABLE 2

| U.S. patent application Ser. No. | Filing Date |
| --- | --- |
| 10/612,109 | Jul. 1, 2003 |
| 10/639,162 | Aug. 11, 2003 |
| 10/672,375 | Sep. 26, 2003 |
| 10/734,547 | Dec. 12, 2003 |
| 10/734,562 | Dec. 12, 2003 |
| 10/735,030 | Dec. 12, 2003 |
| 10/840,950 | May 7, 2004 |
| 10/955,245 | Sep. 29, 2004 |
| 11/070,863 | Mar. 1, 2005 |

Endoscopic tissue grasping devices are described in several of the United States patent applications listed above, and in the following United States patent applications:

TABLE 3

| U.S. patent application Ser. No. | Filing Date |
| --- | --- |
| 11/736,539 | Apr. 17, 2007 |
| 11/736,541 | Apr. 17, 2007 |

Tissue anchors are described in several of the United States patent applications listed above, and in the following United States patent applications:

TABLE 4

| U.S. patent application Ser. No. | Filing Date |
| --- | --- |
| 10/841,411 | May 7, 2004 |
| 11/404,423 | Apr. 14, 2006 |
| 11/773,933 | Jul. 5, 2007 |

Each of the foregoing patent applications is hereby incorporated by reference in its entirety.

I. Endoscopic Ligation

The devices described herein include several embodiments of ligatures and ligature delivery devices that are adapted to carry a ligature to a target site and deploy the ligature on or to the target site. The ligatures and delivery devices are adapted for use during open surgery, laparoscopic surgery, endoscopic surgery, or translumenal surgery. In several preferred embodiments, the delivery device includes a handle, a shaft having a flexible portion, and an end effector adapted to deploy the ligature. The end effector and flexible shaft have a small cross-sectional profile such that the delivery device is able to pass through a small diameter lumen to be routed to a site within a patient's body. In several other embodiments, the delivery device has an elongated, flexible shaft that allows the instrument to be passed through tortuous anatomy, either as a standalone instrument or as an instrument to be passed through a lumen of an overtube. The end effector is be used to engage, grasp, acquire, position, or otherwise manipulate tissue (e.g., an organ, vessel, or other tissue) within a patient. The delivery device is suitable for use as a standalone instrument, or it may be used in combination with other instruments that provide independent or related functions.

In several embodiments, the end effector of the delivery device includes a movable arm or jaw that moves (e.g., rotates) proximally (i.e., toward the handle) upon actuation by the user. For example, in an embodiment, the movable arm rotates around a distal pivot such that the distal-most portion of the arm moves through an arc of between about 90 degrees to about substantially 180 degrees to abut the distal end of the flexible shaft. This "reverse" grasping motion provides several advantages over conventional forward-directed clip applying delivery devices.

Referring to FIGS. 3A-B, a schematic representation of a reverse grasping ligature delivery device 100 is shown. The delivery device shown in FIGS. 3A-B includes a handle 102, a shaft 104, and an end effector 106 attached to the distal end of the shaft 104. In the embodiment shown in FIGS. 3A-B, the end effector 106 includes a fixed arm member 108 and a movable arm member 110. An actuation mechanism 112 is provided at the proximal end of the device in association with the handle 102, and is coupled to the end effector 106 by a drive mechanism that is routed through a lumen defined by the shaft 104. The handle 102 and actuation mechanism 112 serve as an interface for the user to manipulate or control the action of the delivery device 100.

In an embodiment, the shaft 104 is an elongated, flexible member in the form of a sleeve defining an internal lumen. For example, in an embodiment, the sleeve of the shaft 104 is cylindrical, defining an internal lumen in which a rod or wire 114 of the drive mechanism is located. The rod or wire 114 is longitudinally translatable within the sleeve, preferably slidably, thereby providing the capability for the shaft sleeve and the rod or wire 114 of the drive mechanism to move longitudinally relative to one another.

The shaft 104 is adapted to provide a flexible, operable interconnection between the handle 102 and the end effector 106. In an embodiment, the shaft 104 is formed of materials having sufficient strength and other material properties to support transmission of torque forces between the handle 102 and the end effector 106. For example, the sleeve portion of the shaft 104 is capable of causing the end effector 106 to rotate around the longitudinal axis of the shaft 104 in response to a rotation of the handle 102. In an embodiment, the sleeve portion of the shaft 104 also supports relative sliding movement of the wire or rod 114 of the drive mechanism within the sleeve with very little friction and without a large amount of longitudinal stretch or compression.

In an embodiment, the sleeve of the shaft 104 is constructed of a single material. In another embodiment, the sleeve has a composite construction that includes two or more of a main body material to provide structure and flexibility, a reinforcing material to provide torque transmission capability and/or to reduce or eliminate stretch and contraction, and a liner material to reduce friction and/or to reduce or eliminate stretch and contraction. Examples of materials that are suitable for forming the main body portion of the external sleeve include polymeric materials, such as polyester amide block copolymer (PEBAX™), nylon, polyurethane, or other similar materials commonly used for medical instrument applications. Examples of suitable reinforcing materials include polymeric or metallic braid materials and/or reinforcing wires. Examples of suitable liner materials include polytetrafluoroethylene (PTFE), polyetheretherketone (PEEK), or other suitable materials.

The wire or rod 114 of the drive mechanism is adapted to transfer a longitudinally-directed force applied by the user from the actuation mechanism 112 on the handle 102 to the end effector 106. In the embodiment shown in FIG. 6, the wire or rod 114 is formed of a single solid wire, coiled wire, or similarly-shaped member that extends through the length of the lumen formed by the sleeve of the shaft 104. As described above, the wire 114 and sleeve are adapted to move longitudinally relative to one another. In an embodiment, the wire 114 is a wire formed of stainless steel, nickel titanium alloy (Nitinol), or other material commonly used for medical instrument applications. In other embodiments, the wire 114 is formed of non-continuous segments aligned end-to-end and joined together to provide the desired longitudinal translation force. In still other embodiments, the wire or rod 114 comprises two or more continuous or non-continuous wires, rods, or similarly-shaped members. In some embodiments, the two or more members are arranged coaxially within the sleeve of the shaft 104, while in other embodiments the two or more members are aligned alongside one another.

The handle 102 is configured to provide the user with an interface to control gross movement of the delivery device 100, and the actuation mechanism 112 is configured to provide relative movement between the sleeve of the shaft 104 and the wire or rod 114 associated with the shaft 104. Several common types of medical instrument handles and actuation mechanisms are suitable for this purpose, including squeeze handles, ring handles, syringe-type handles, pistol grips, and others known to those skilled in the art. Additional handle embodiments are described in, for example, U.S. patent application Ser. Nos. 11/736,539 and 11/736,541, each filed Apr. 17, 2007, and U.S. Pat. Appl. Ser. No. 61/012,742, filed Dec. 10, 2007, each of which is incorporated by reference herein in its entirety. In still other embodiments, the actuation mechanism 112 includes an indexing mechanism used to activate the end effector 106 to one or more predetermined positions. In still other embodiments, the actuation mechanism 112 includes a locking mechanism to selectively lock the end effector 106 in a selected position.

Turning to FIG. 4, an end effector 106 of a delivery device is shown. The fixed arm member 108 is located at the distal end of and is formed integrally with the shaft 104. The proximal end of the movable arm member 110 is attached to the distal end of the fixed arm member 108 by a pivot pin 116. This construction allows the movable arm member 110 to transition from an open state in which the movable arm member 110 is in line with and extends distally from the distal end of the fixed arm member 108 (shown in shadow in FIG. 4), toward a closed state in which the movable arm member 110 rotates around the pivot pin 116 (as indicated by arrow "A") toward the fixed arm member 108. The amount of rotation of the movable arm member 110 will depend upon several factors, including at least the beginning orientation and the presence, type, size, and shape of a target tissue in the space between the fixed arm member 108 and the movable arm member 110. Preferably, the movable arm member 110 rotates at least about 90 degrees, more preferably at least about 120 degrees, and up to about 180 degrees. This "reverse grasping" motion causes the movable arm member 110 and fixed arm member 108 to come into apposition relative to one another, thereby creating and defining a clip deforming space therebetween. A ligation clip 120 positioned between the two arm members 108, 110 is squeezed by the motion of the movable arm member 110 to deform the clip 120 for application.

The reverse grasping orientation of the delivery devices 100 described herein provides a number of advantages over a conventional forward-facing (i.e., distally oriented) clip applier. Referring once again to the clip applier 50 shown in FIGS. 1A-B, as the clip applier 50 is placed into position, the jaws 54 face distally, i.e., away from the visualization field provided by an endoscope located proximally of the jaws 54. This orientation prevents the user from being able to visualize the jaws 54 and the clip as the clip is applied to the tissue T. In addition, this orientation requires the user to advance the clip applier distally, toward the target tissue, in order to acquire the tissue in the space between the jaws 54. It is often difficult to cause the target tissue to seat deeply within the jaws 54 when this motion is used.

On the other hand, the reverse grasping delivery device shown in FIGS. 3A-B includes a fixed arm 108 and movable arm member 110. Transitioning the movable arm member 110 from the open position toward the closed position causes the end effector 106 to take on a "hook" shape, as illustrated in FIGS. 3A-B. The hook shape allows the user to approach the target tissue from the distal side and retract the delivery device in order to cause the tissue to seat deeply within the compression space between the fixed arm 108 and movable arm 110, as shown in FIG. 3B. This motion is also illustrated in FIGS. 5A-C, where the delivery device is first advanced distally past the site of the target tissue T (as shown in FIG. 5A), then retracted proximally to capture the tissue T in the space between the fixed and movable arm members 108, 110

Figure 5B:
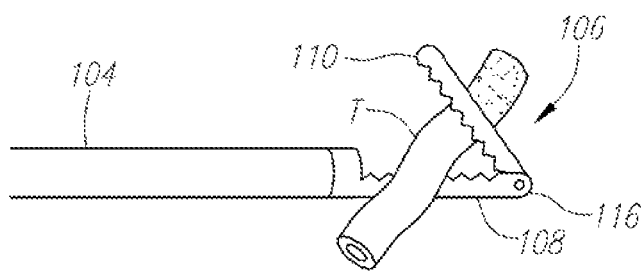
Figure 5C:
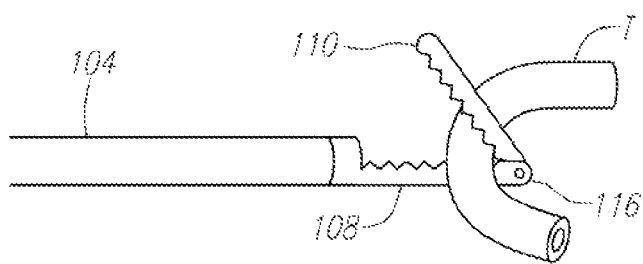

(as shown in FIG. 5B), and finally retract the delivery device further proximally in order to seat the tissue T deeply within the compression space prior to deploying a ligature device (as shown in FIG. 5C). (Note that the ligature device is omitted from FIGS. 5A-C for clarity). Once the tissue T is thus acquired, the movable arm member 110 is fully actuated to compress and deploy the ligature device (e.g., a ligating clip 120). The retracting motion used to acquire and seat the tissue between the arm members is advantageous because it allows the user to skeletonize or strip away connective tissues or fat by simply using the open jaw as a scraper. The "hook and close" capability also reduces the frequency of tissue slipping out from between the arm members during the closing process.

The reverse grasping orientation also improves visualization from, e.g., an endoscope located proximally of the end effector 106. As noted above, with a conventional clip applier 50 the tips of the jaws 54 are not visible. However, with the reverse grasping delivery device 100, the tip of the movable jaw 110 is brought directly into the visual field during the ligature deployment procedure. The user is thereby able to confirm that the ligature has been applied safely and securely.

Figure 6:
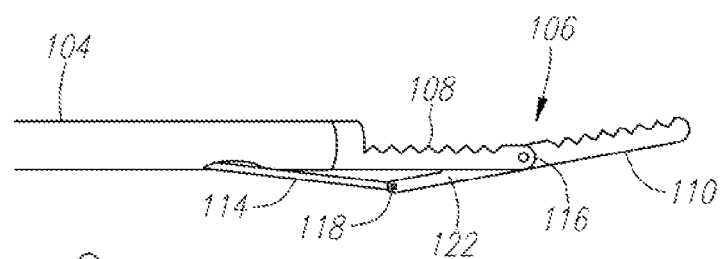
FIG. 6 is a side view of another embodiment of a reverse grasping ligature delivery device.

An embodiment of a drive mechanism for a reverse grasping delivery device 100 is shown in FIG. 6. The movable arm member 110 is attached to the fixed arm member 108 by a first pivot 116. An arm lever 122 extends from the movable arm 110 on the side of the pivot pin 116 opposite of the movable arm member 110, where it is attached to the drive rod 114 by a second pivot pin 118. As the drive rod 114 is advanced distally (e.g., via actuation of the actuation mechanism 112 on the handle 102), the rod 114 forces the arm lever 122 to rotate counterclockwise (as shown in FIG. 6), thereby rotating the movable arm 110 toward the fixed arm member 108 toward the closed (or compressing) position. Similarly, retraction of the rod 114 causes the movable arm member 110 to transition from the closed position toward the open position.

Figure 7A:
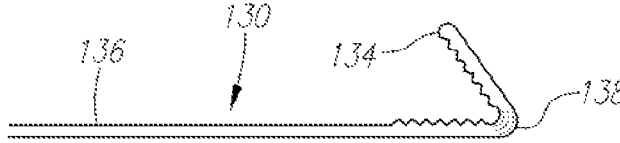
FIGS. 7A-B are side views of a hinged insert and a sliding sleeve for another embodiment of a reverse grasping ligature delivery device.
Figure 7B:
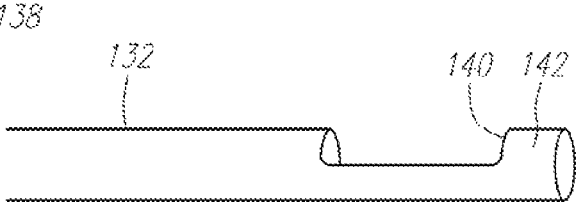
Figure 7C:
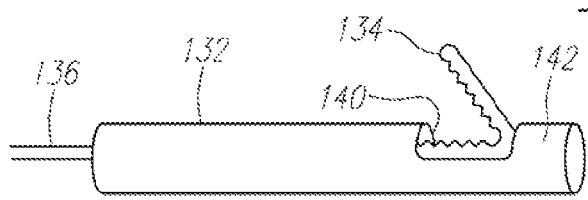
FIG. 7C is a side view the reverse grasping ligature delivery device corresponding to the components shown in FIGS. 7A-B.

Another embodiment of a drive mechanism for a reverse grasping delivery device 100 is shown in FIGS. 7A-C. In this embodiment, the end effector 106 includes a jaw assembly 130 and a separate housing assembly 132. The jaw assembly 130 includes a movable jaw 134 located at the distal end of a shaft member 136 of the jaw assembly 130. A living hinge 138 connects the movable jaw 134 to the shaft 136. The living hinge 138 is biased such that it will spring to the open position unless under a force or load. The jaw assembly 130 is preferably formed of spring steel or nitinol to provide resilience and strength. The housing assembly 132 is generally tubular and includes a cutout 140 located near the distal end of the housing assembly 132.

Turning to the fully assembled device, shown in FIG. 7C, as the jaw assembly 130 is advanced distally within the housing assembly 132, the movable jaw 134 is first able to extend outward through the cutout 140 to define a hook shape that is able to acquire and manipulate tissue T. As the jaw assembly is advanced further distally, the living hinge 138 is engaged by a closure collar 142 formed by the housing at a point distally of the cutout 140. The engagement by the closure collar 142 causes the movable arm 134 to rotate about the living hinge 138 toward the shaft 136. This reverse grasping motion is suitable for deploying a ligature device, such as a clip 120 (not shown in the drawing for clarity).

Turning next to FIGS. 8A-C and 9A-C, the reverse grasping motion of the delivery devices 100 described herein facilitates advantageous methods for deploying and forming ligature devices, such as ligating clips. In the embodiments shown, a plurality of ligating clips 120 are loaded flat, end-to-end, in a longitudinal channel 150 of the delivery device 100. As shown in FIGS. 8A and 9A, the movable arm member 110 is initially placed in the fully open position, i.e., extended distally from the distal end of the fixed arm member 108. A first clip 120 is advanced out of the distal end of the channel 150 by way of a pusher or other suitable advancement mechanism. Once the clip 120 is advanced into position, the movable arm member 110 is actuated to rotate proximally toward the fixed arm member 108, as shown in FIGS. 8B and 9B, under control of the actuation mechanism 112. (Note: For clarity, the drive mechanism is not shown in FIGS. 8A-C and 9A-C). As the movable arm member 110 rotates, it causes the clip 120 to become bent into a deployed configuration. The device is moved in order to acquire a target tissue T, as shown in FIG. 8B, after which the movable arm member 110 is actuated to its full deployment state, thereby compressing the clip 120 onto the target tissue T. Once the clip 120 is fully compressed, the movable arm member 110 is transitioned back into its open state, as shown in FIG. 8C, thereby releasing the deployed clip 120.

In some embodiments, as shown in FIG. 10, the deployed clip 120 includes a first leg 120a that is slightly longer (e.g., by a distance Δ) than the second leg 120b. The longer leg 120a is thereby able to be retained temporarily within the channel 150 prior to release from the delivery device 100. Full release is achieved by advancing another flat clip through the channel 150 to force the first clip 120 out of the device.

Figure 11A:
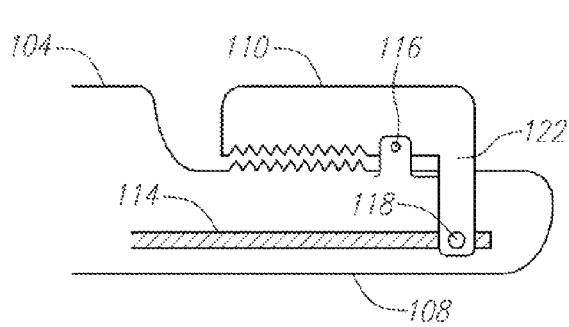
FIGS. 11A-B are side cross-sectional views of another embodiment of an end effector of a reverse grasping ligature delivery device.
Figure 11B:
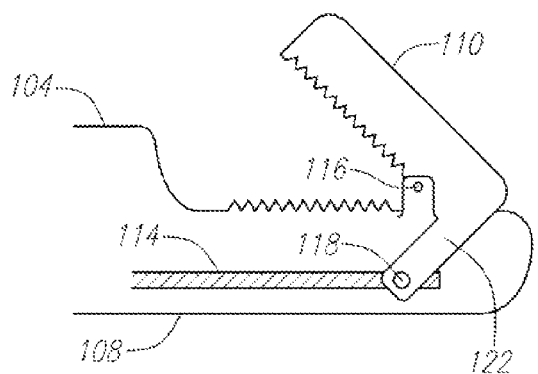
Figure 12A:
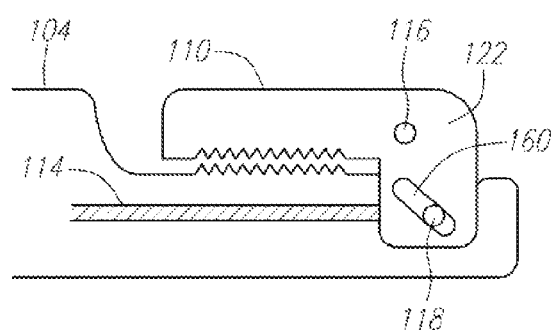
FIGS. 12A-B are side cross-sectional views of another embodiment of an end effector of a reverse grasping ligature delivery device.
Figure 12B:
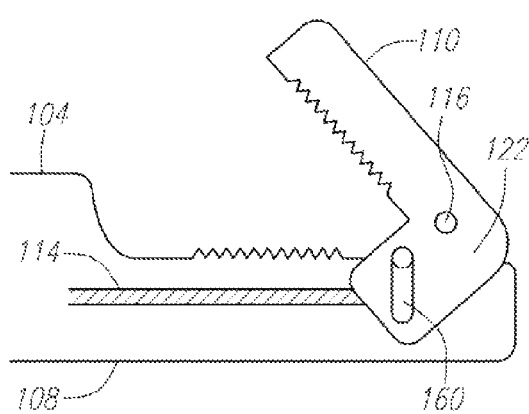

Several alternative orientations of the end effector 106 and drive mechanism of the delivery devices are shown in FIGS. 1A-B, 12A-B, 13A-B, 14A-B, and 15A-B. In a first embodiment, shown in FIGS. 11A-B, the drive rod 114 is attached to the arm lever 122 by a second pivot pin 118, with the second pivot pin 118 being located at a point that is distal of the first pivot pin 116. In this orientation, proximal retraction of the drive rod 114 causes the movable arm member 110 to rotate clockwise (i.e., to transition to the "open" position), whereas distal advancement of the drive rod 114 causes the movable arm member 110 to rotate counterclockwise (i.e., to transition to the "closed" position). Accordingly, the drive mechanism orientation shown in FIGS. 11A-B corresponds with a "pull-open" "push-close" actuation. The embodiments shown in FIGS. 12A-B are also "pull-open" and "push-close." The FIGS. 12A-B embodiments include a pivot slot 160 formed in the arm lever 122, in which the second pivot pin 118 is able to slide in order to reduce the amount of transverse movement of the drive rod 114 during actuation and allow the drive rod 114 to remain substantially within a single plane.

Figure 13A:
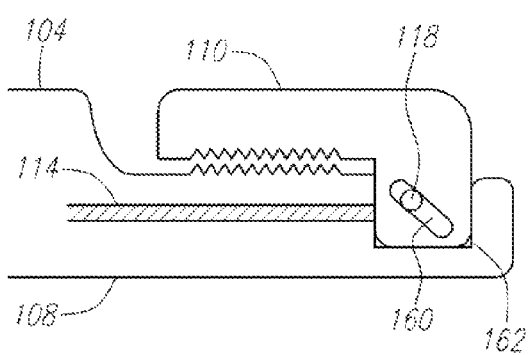
FIGS. 13A-B are side cross-sectional views of another embodiment of an end effector of a reverse grasping ligature delivery device.
Figure 13B:
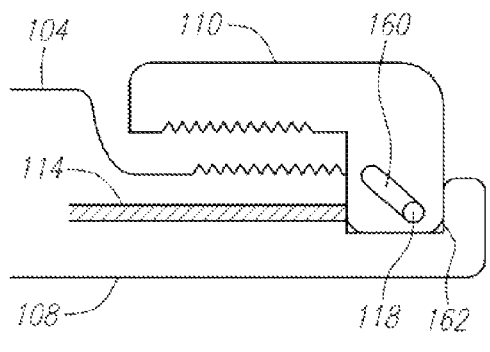

The embodiments shown in FIGS. 13A-B do not include a first pivot pin 116. Instead, the movable arm member 110 is able to translate up and down relative to the fixed arm member 108 within a track 162 defined by the fixed arm member 108. Proximal retraction of the drive rod 114 causes the movable arm member 110 to move downward—i.e., toward the fixed arm member 108—whereas distal advancement of the drive rod 114 causes the movable arm member 110 to raise upward—i.e., away from the fixed arm member. This motion is controlled by the movement of the second pivot pin 118 within the pivot slot 160 formed in the arm lever 122, as shown in the Figures. With these motions, the embodiments shown in FIGS. 13A-B provide "pull-close" and "push-open" actuation.

Figure 14A:
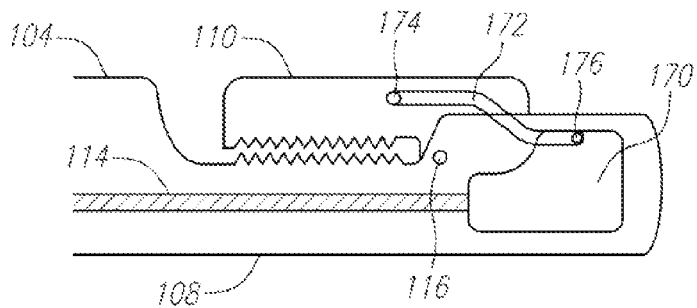
FIGS. 14A-B are side cross-sectional views of another embodiment of an end effector of a reverse grasping ligature delivery device.
Figure 14B:
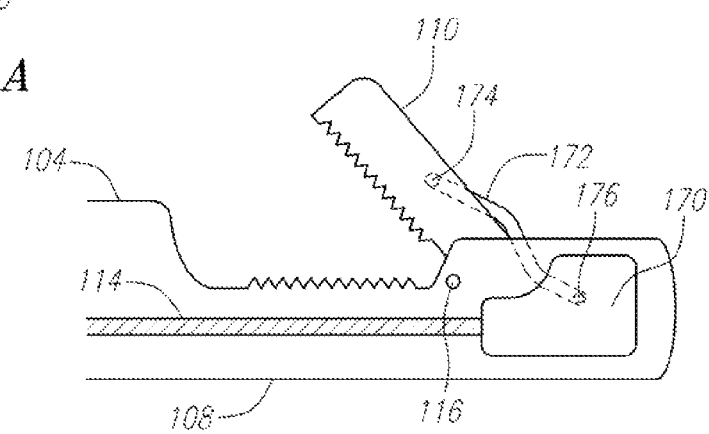
Figure 15A:
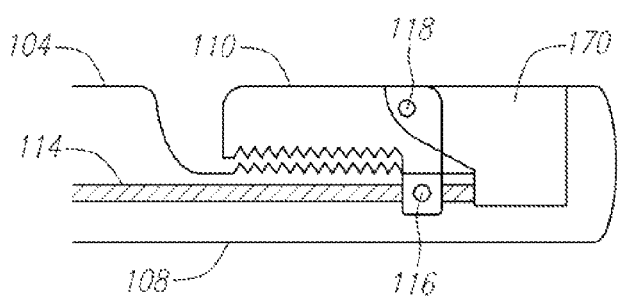
FIGS. 15A-B are side cross-sectional views of another embodiment of an end effector of a reverse grasping ligature delivery device.
Figure 15B:
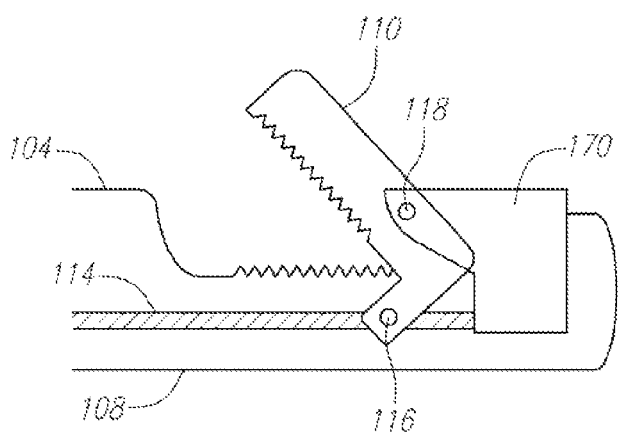

Turning to FIGS. 14A-B, the drive rod 114 is attached to a drive block 170 at the distal end of the device. An offset lever 172 extends between and connects the drive block 170 to the movable arm member 110 via a third pivot pin 174 (connecting the offset lever 172 to the movable arm member 110) and a fourth pivot pin 176 (connecting the offset lever 172 to the drive block 170). The FIGS. 15A-B embodiment is similar, but does not include the offset lever—i.e., the drive block 170 is directly attached to the movable arm member 110 by way of a pivot pin 118. In these embodiments, distal advancement of the drive rod 114 causes the drive block 170 to move distally, which motion is translated into clockwise rotation of the movable arm member 110 (i.e., toward the "open" position shown in FIGS. 14B and 15B). Proximal retraction of the drive rod 114, on the other hand, causes proximal motion of the drive block 170, which motion is translated into counter-clockwise rotation of the movable arm member 110 (i.e., toward the "closed" position shown in FIGS. 14A and 15A).

Persons skilled in the art will recognize that other variations of drive mechanisms are possible to achieve the objective of translating an actuation force at the handle 102 into rotational movement of the movable arm member 110 at the end effector 106 of the device.

Figure 16A:
FIGS. 16A-C are side views of another embodiment of a ligature device.
Figure 16B:
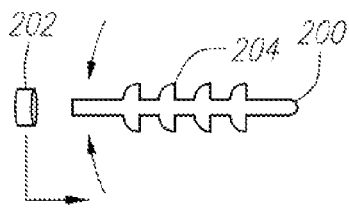
Figure 16C:
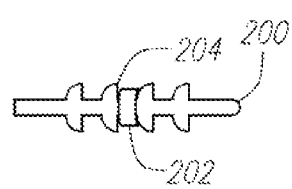

Turning next to FIGS. 16A-C, an alternative embodiment of a ligature device is shown. The ligature device includes a "U" shaped ligation clip 200 and a locking collar 202 that slides over the legs of the clip to complete full encirclement. The clip 200 does not require permanent deformation to maintain its hold as the locking collar 202 also functions to hold the clip legs together. This allows a wider opening of the clip 200 since the clip can be of a relatively flexible or even super elastic material.

The delivery device 210 for this ligature device embodiment is another embodiment of a reverse grasper device such as those described above. The reverse grasper orientation allows the user to "hook" the target tissue and pull back to ensure the tissue is entrapped fully while applying the final locking with the collar 202 under direct visualization.

In the embodiment shown in FIGS. 16A-C, the collar 202 is made from a section of hypodermic tubing and the clip 200 is formed from a metal wire or ribbon. It is preferred that the clip be made of nitinol and the collar is of nitinol or titanium. The clip 200 is formed into an open "U" shape or, alternatively, is completely open with both legs having an included angle of 180 degrees. The clip 200 is shaped with engagement features 204 that allow the collar 202 to slide on with a delivery system but not easily slide off. In an embodiment, these are macroscopic ratchet type features 204 as shown in the Figures. Alternatively, the engagement features are microscopic surface treatment features. In an embodiment, the surfaces of the two components are sufficient to keep the collar 202 from sliding off after its application. In an embodiment, the engagement features 204 also serve the purpose of holding onto tissue T on the inner surface of the clip legs. FIG. 16B shows the clip 200 closed by an external force and the collar 202 positioned to slide onto the closed legs. FIG. 16C shows the clip 200 positioned at one of the numerous/continuous final positions, thus maintaining the clip closure and closing the clip into a closed path.

Figure 17A:
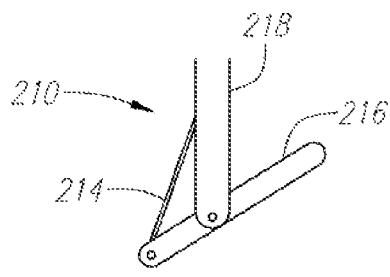
FIGS. 17A-B are side views of another embodiment of an end effector of a reverse grasping ligature delivery device.
Figure 17B:
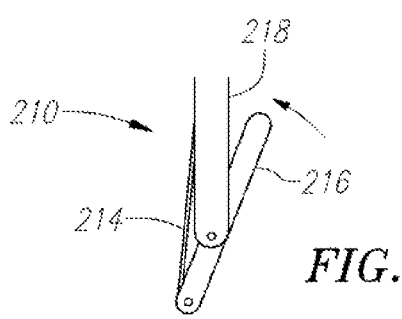

FIGS. 17A-B show a schematic of a delivery device 210 suitable for delivering the ligation clips 200 described above. In this embodiment, the delivery device 210 includes a linkage system 212. An actuation rod 214 is advanced and retracted to cause a jaw 216 to open and close against the shaft 218 or a second jaw. In an embodiment, the jaws are able to be actuated into a nearly in line (included angle 180 degrees) position suitable for tissue engagement. The in line jaws are then slid into a crevice or under a portion of tissue in a low profile position and then actuated to wrap around and over the target tissue.

Figure 18A:
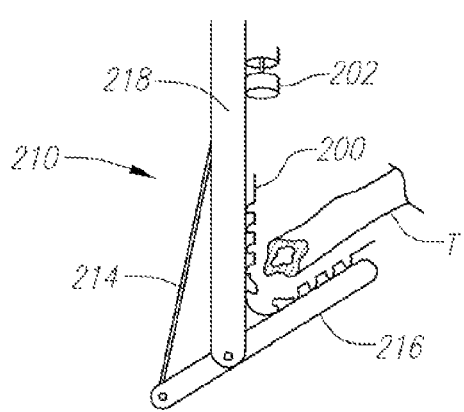
FIGS. 18A-B are side views of another embodiment of an end effector of a reverse grasping ligature delivery device showing a deployment of a ligature device.
Figure 18B:
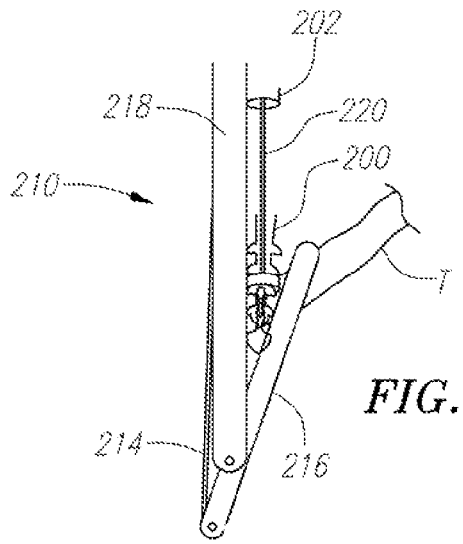
Figure 19:
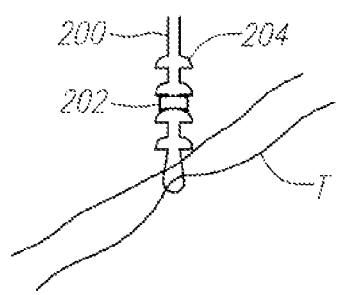
FIG. 19 is a perspective view of another embodiment of a ligature device deployed on a portion of tissue.
Figure 31A:
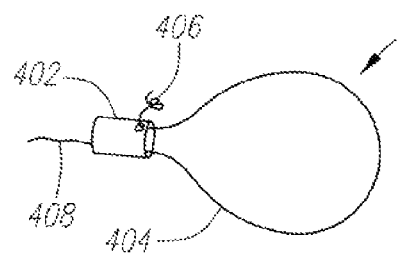
FIGS. 31A-C include perspective views of an embodiment of a lasso type ligature device.
Figure 31B:
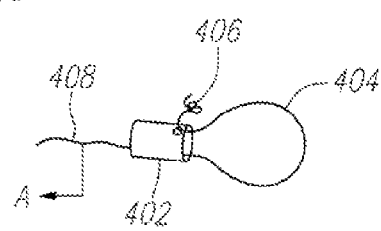
Figure 31C:
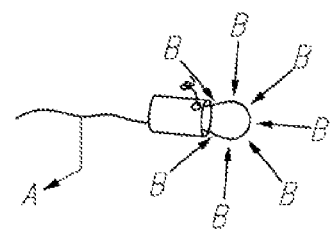
Figure 32A:
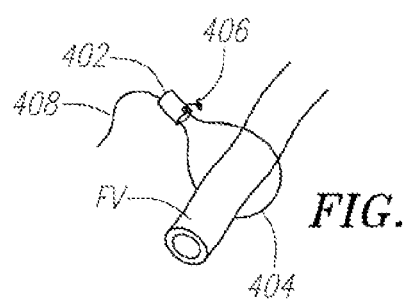
FIGS. 32A-B and 33A-B show deployments of embodiments of lasso type ligature devices.
Figure 32B:
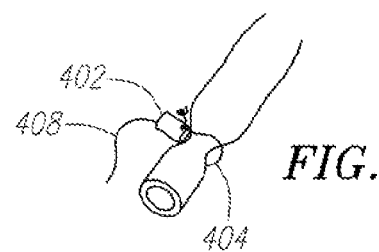

FIGS. 18A-B show the ligature device 200 being deployed with the delivery device 210. The clip 200 is held by press fit hooks or a positively engaging clamping feature. One leg of the clip is held on the moving jaw 216. The other leg is held on the stationary shaft/jaw 218. The delivery device 210 is activated to reversibly open and close the clip 200. The locking collar 202 is held on a breakaway delivery rod 220 adjacent to the clip 200. Preferably, the locking collar 202 is directed so that a linear forward motion will drive the collar 202 over the legs of the clip once closed. FIG. 18B shows the delivery device 210 activated to entrap a vessel T and the locking collar 202 positioned over the clip legs. FIG. 19 shows the applied ligation clip 200 and collar 202 on a vessel T with the delivery device removed.

In several of the foregoing embodiments, the delivery devices 100 and 210 described herein are configured to work through existing endoscopes as an instrument or accessory. Accordingly, in some embodiments, the devices have a transverse dimension of no larger than 3 mm to fit the majority of conventional endoscope tool channels having working lumens. The medical instrument is also provided with a flexible shaft, and the end effector is preferably flexible and has a minimal rigid length to facilitate loading and removal from the scope.

In several others of the foregoing embodiments, the delivery devices 100 and 210 described herein are configured to work through a working channel or lumen of an endoscopic or translumenal access device as an instrument or accessory. Several of these access devices are described in the patent applications contained in Table 1 above, and are described in more detail below. Accordingly, in some embodiments, the devices have a transverse dimension of no larger than about 10 mm, and preferably between 3 mm to about 7 mm, in order to fit the working channels of the access devices. The devices are also provided with a flexible shaft, and the end effector is preferably flexible and has a minimal rigid length to facilitate loading and removal from the access device.

II. Ligatures

Several alternative embodiments of ligature devices are described below. The ligature devices are suitable for delivery and deployment endoscopically, including through the use of flexible endoscopic access and delivery devices. For example, in some embodiments, the ligature devices are delivered and deployed using delivery devices that are advanced through one or more channels of a conventional endoscope. In several other embodiments, the ligature devices are delivered and deployed using the delivery devices described in the preceding section and in Table 1 above.

Additional ligature device embodiments are shown in FIGS. 20A-B through 25. The illustrated embodiments include a finger snare device 300 having an expandable loop 302 with a cooperating wire or ribbon 304 configured to interlock with the loop. The loop 302 and ribbon 304 are formed of a medical grade material, such as a plastic or other polymeric material, or a metal or metallic material. For example, in some embodiments, the loop 302 and ribbon 304 are made from multifilament cable, coils, or combinations of the foregoing. In a preferred embodiment, the loop 302 and ribbon 304 are made of superelastic nitinol wire.

The operation of the finger snare device is as follows. The loop 302 and ribbon 304 are shaped and attached such that the loop 302 defines a plane. The ribbon 304 is formed into generally an "L" or hook shape. The ribbon 304 is positioned such that the plane of its shape is perpendicular to the plane of the loop 302. In an embodiment, the finger snare assembly 300 is retracted into a tube or collar 306. This motion causes the ribbon 304 to fold forward and into the loop 302. The motion also causes the loop 302 to be compressed. The ribbon 304 is sized such that its length when straightened is longer than the length of the loop 302 when compressed and straightened. The schematic representations in FIGS. 21A-B illustrate the operation. The ribbon/loop interaction is shown in free space (FIG. 21A) and on a vessel (FIG. 21B). In alternative embodiments, illustrated in FIG. 22, the interlocking of the ribbon 304 and loop 302 is augmented with the addition of an interlocking feature on the ribbon such as, for example, a hook 310, a ball 312, or a catch 314. These interlocking features also inhibit or prevent the loop and wire from becoming separated.

An embodiment of an activatable and releasable finger snare 300 is shown in FIG. 23, and its deployment is shown in FIG. 24. The ligature device includes a ribbon/loop assembly 300 slidably housed within a closure sleeve 306. The components cooperate to close and maintain the ligation. The closure sleeve 306 slides in one direction over the ribbon 304 and loop 302 thereby causing the finger snare device 300 to activate. The motion is performed by a releasable activation rod 320 and an anvil coil 322. The ligation assembly is lightly press-fitted on the anvil coil 322 with the activation rod 320 running thru the coil 322. A distal end of the activation rod 320 is provided with a crossbar 321 that is adapted to releasably seat within a notch 303 formed on a base portion 301 of the ligation assembly. By retracting the activation rod 320, the ribbon 304 and loop 302 assembly is retracted into the closure sleeve 306. This motion is continued until sufficient ligation occurs. After the ligator assembly is activated onto the tissue, the ligation assembly 300 can then be forced off the activation coil 322 by pushing forward on the activation rod 320. Once free of the coil 322, the ligation assembly 300 and activation rod 320 are de-coupled by simply having the mechanical interlock between the crossbar 321 and notch 303 slide apart. This whole combination can initially be housed in a placement sleeve 324 that maintains the ligature in a low profile.

The finger snare ligature 300 may be fabricated in a variety of ways. For example, in several embodiments, machined parts are used to fabricate the device. In other embodiments, bent wires are used. Several embodiments include fabrication out of tubing and laser cutting. The wire loop 302 can be cut from a single piece of nitinol tubing and then formed into its shape memory condition. The activation sleeve 306 could also be made from a nitinol cut tube where a metal tab 307 is cut and shaped to point into the lumen to act as the one way retention feature. An example of a flattened pattern to create the ribbon/loop structure is illustrated in FIG. 25.

Additional ligature device embodiments are shown in FIGS. 26A-B. These embodiments include an elongated strip 332 having a plurality of engagement features 334. The ligature 330 is carried to the target site by an applicator 340. The applicator 340 includes a crooked or arcuate shaped track 342 on the end of an elongated shaft 344. The crooked/arcuate track 342 is positioned so as to partially encircle the target. The strip 332 is then advanced and follows a path defined by the crooked/arcuate applicator track 342. Continued advancement of the strip 332 causes the strip to slide so that it spans a gap 346 defined by the track (as shown in FIG. 26B), at which point the strip 332 is looped back upon itself. An engagement block 350 is located near the distal end of the applicator 340, just proximal of the crooked/arcuate track 342. The strip 332 runs through the engagement block 350 and returns into the engagement block 350 after it completes its return path. The engagement block 350 retains the strip 332 in its constricted loop shape. In the embodiments shown, the engagement block 350 includes a ratchet mechanism that engages a row of teeth formed on a facing surface portion of the strip. Other engagement mechanisms would also be suitable.

In an alternative embodiment, shown in FIG. 27, a hook or grasper 352 is used to reach across the crook's span 346 to acquire the strip 332. The grasper 352 is then withdrawn to pull the strip 332 through a retention feature 350. This embodiment allows constriction of the strip 332 to a smaller circumference than the track 342. The retention feature 350 can be integral to the strip 332 or a separated component that is fixed on the end of the strip 332 and through which the tip of the strip 332 can be threaded with the grasper 352.

Still other ligature devices and methods are shown in FIG. 28. As discussed earlier herein, USGI Medical Inc. has several patent applications that describe tissue anchors and devices and methods for delivering multiple anchors on a connecting filament. See, for example, U.S. patent application Ser. Nos. 10/612,109, filed Jul. 1, 2003; 10/612,170, filed Jul. 1, 2003; 11/404,423, filed Apr. 14, 2006; and 11/773,933, filed Jul. 6, 2007. Each of the foregoing applications is hereby incorporated by reference in its entirety. In several examples of these devices and methods, the assembly has a one-way cinching feature that allows the anchors to be driven and held in apposition. See also, for example, U.S. patent application Ser. No. 11/036,946, filed Jan. 14, 2005, which is also hereby incorporated by reference in its entirety. In the present embodiment, two or more anchors 360a, 360b function as opposing halves of a vessel clip. The anchors 360a, 360b are delivered on opposing sides of a vessel V by a needle catheter 366, and then driven to close approximation to constrict the vessel V, as illustrated in FIG. 28. Once approximated, the anchors 360a, 360b are maintained in place by a one-way cinch 362 carried on a suture 364 connecting the two anchors 360a, 360b.

Another embodiment of the opposing anchors includes a pair of anchors 370a, 370b that are shaped to interface so that they can maintain a grasp on a vessel V even if they are not actually anchored through the vessel. This embodiment is suitably deployed in the direct vicinity of a vessel V and then opposed to capture and ligate. An example includes two anchors 370a, 370b that are concave, as shown in FIG. 29. Also, a pair of anchors 380a, 380b including multiple concave struts, like an umbrella frame, is suitable in that it allows numerous orientations for performing the ligation function, as shown in FIG. 30.

Other ligature device embodiments are described below and illustrated in FIGS. 31A-C through 37A-B. For example, in FIGS. 31A-C, a "lasso" style ligature device 400 is shown. The device includes a collar 402 and a continuous strand of a flexible suture or other flexible, medical grade material defining a loop 404. A first free end of the loop 404 is threaded through a hole formed in a sidewall of the collar 402 and includes a knot 406 (or other form of stop) to prevent the free end of the loop 402 from pulling through the hole. A second free end 408 of the loop is threaded through the collar 402. The collar 402 includes a one-way cinching mechanism 420 (see FIG. 35) that allows the second free end 408 to be advanced in the direction of arrow "A" (see FIGS. 31B-C), but that prevents movement of the loop in the opposite direction. In this manner, the loop 404 is able to be constricted, as shown by the arrows "B" in FIG. 31C, but, once constricted, the loop 404 is not able to re-expand. This provides positive ligation.

Figure 33A:
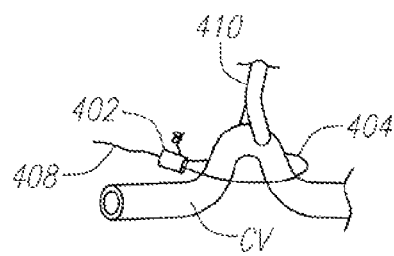
Figure 33B:
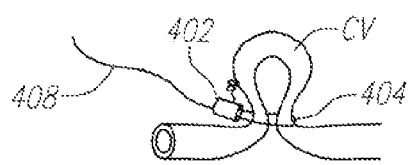

The "lasso" style devices are suitable, for example, for positioning over target sites that have an exposed cut end for the device to be slid over. For example, FIGS. 32A-B and 33A-B show a schematic of the device as applied to: (a) a free end vessel "FV" (FIGS. 32A-B) and (b) a continuous vessel "CV" (FIGS. 33A-B). The lasso device 400 is suitable for use over a continuous vessel or over a span of tissue or vessel if a convolution or "mound" is drawn up into the loop (such as by a grasper 410), as illustrated in FIGS. 33A-B.

Figure 34:
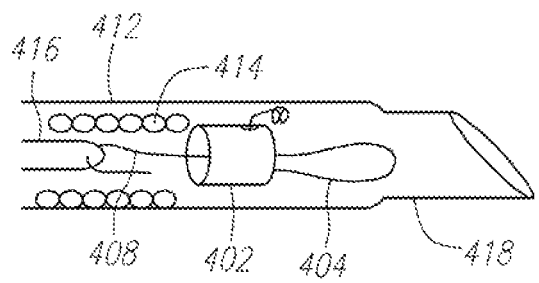
FIG. 34 includes a side view of an embodiment of a lasso type ligature device and a portion of an embodiment of a delivery mechanism.
Figure 35:
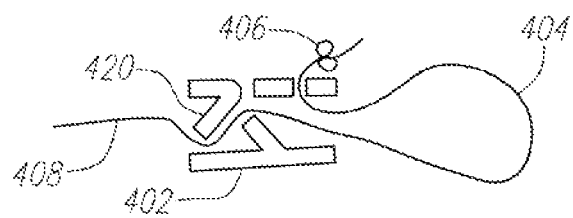
FIG. 35 includes a cross-sectional view of an embodiment of a lasso type ligature device.

Additional details of the "lasso" style ligature device embodiment are illustrated in FIGS. 34 and 35. In some embodiments, the ligature device 400 is delivered with a catheter 412, pusher 414, and releasable loop 416 delivery system such as the delivery systems developed by USGI Medical Inc. In an embodiment, the ligature device is suitably delivered using a g-Prox™ plication device, developed and manufactured by USGI Medical Inc., in the following manner. The g-Prox™ device is used to articulate the lasso ligature so that the ligature is applied at an angle, or even perpendicular, to the tissue. The g-Prox™ device and lasso assembly 400 may be used in conjunction with the multi-lumen TransPort™ translumenal access device, thereby providing the ability to apply one or more secondary tools, such as a grasper. This assembly facilitates the ligation of an uncut vessel as shown, for example, in FIGS. 33A-B. In another embodiment, the loop 404 is bolstered with a non expandable or expandable anchor. In still other embodiments, the lasso ligature device is delivered through a needle catheter 418. The lasso is then applied on a target and linked to another tissue site.

Figure 36A:
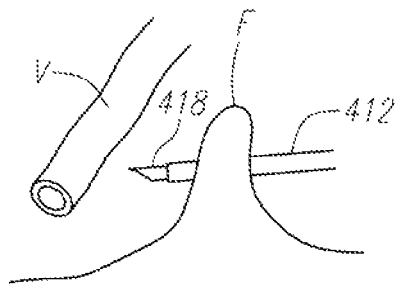
FIGS. 36A-B and 37A-B show deployments of embodiments of lasso type ligature devices.
Figure 36B:
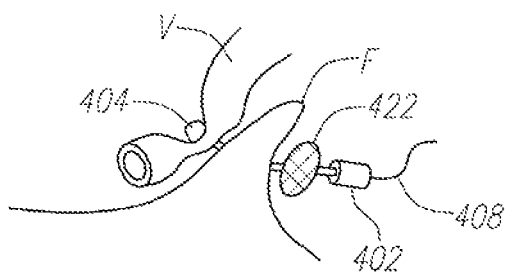
Figure 37A:
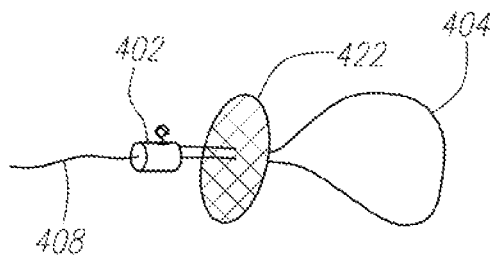
Figure 37B:
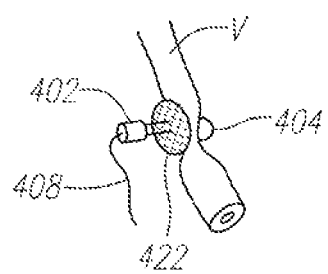

The embodiments shown in FIG. 34 illustrate a lasso style ligature device in a delivery catheter having the capability to be deployed and tightened. The embodiment shown in FIGS. 37A-B illustrate a lasso style ligature device 400 having a tissue anchor 422 as part of the assembly. The embodiment shown in FIGS. 36A-B illustrates a lasso style ligature device 400 and an anchor 422 used to ligate a vessel V and bring it into apposition with a tissue fold F.

Additional ligature devices and methods are shown in FIGS. 38A-B through 41. A clip 430 is constructed such that it requires no mechanical deformation to be deployed. For example, a "U" clip 430 is made from shape memory nitinol. The clip 430 is pre-shaped into a closed clip configuration, as shown in FIG. 38B. An applier device 432 is constructed such that it is able to open the clip 430, release it, and allow it to spontaneously form to its closed shape around a vessel V. An embodiment of the clip device 430 is shown in FIG. 39. The clip 430 is preferably formed of a nitinol tube. The clip 430 has one or more opening(s) 434 that allow insertion of one or more straightening rods(s). The straightening rod(s) function as a backbone to keep the clip in its open configuration. Upon withdrawal of the rods, the clip 430 transitions to a closed configuration. Upon complete removal of the rods, the clip transitions to its fully closed configuration and is released from the applier 432.

The schematic illustrations in FIG. 40 show a delivery catheter 432 configured with two rods 436, 438 that exit thru a side port 440. One rod 436 is straight, the other rod 438 is bent into a hook shape. The tube clip 430 is initially held and straightened by the rods. A twist knob 442 on the user end moves both rods equally and simultaneously in opposite directions. This causes the straight rod 436 to pull back and the hooked rod 438 to drive forward. This in turn moves both rods free of the tube clip 430. The clip 430 is thereby formed and released.

In several embodiments, the tube clip is fabricated with additional features. For example, in several embodiments, two openings 434 are provided for the activation rods and/or slots cut into or through the tube surface to create textures or gripping surfaces. These features are illustrated in FIG. 39.

In other embodiments, the clip is formed into a "U" or "V" or other shapes. For example, in some embodiments, the clip is formed into an opposing spiral shape. This shape reduces or eliminates any protrusions in the deployed shape and/or the motion of the spirals forming could help to draw tissue into the grasp of the clip, as illustrated in FIG. 41.

Turning to FIGS. 42-44, additional ligature device embodiments are shown. The devices include a potential energy deployment mechanism, i.e., a stored energy mechanism that causes the device to transition to a deployment (ligating) mode when the stored energy is released. For example, in FIG. 42, the device 450 includes a pair of arms 452, 454 extending from a torsion spring 456. In FIG. 43, the device 460 also includes a pair of arms 462, 464 extending from a torsion spring 466. In FIG. 44, the device 470 includes a pair of arms 472, 474 extending from a bridge member 476, and the device is formed of a material having a high elasticity value to provide a "spring" effect. Each of these devices is constructed such that the spring force biases the arms to a closed, or deployment position in which a target tissue or vessel is able to be ligated between the pair of arms.

The devices shown in FIGS. 42-44 are suitable for delivery using a reverse grasper delivery device, such as those described above. For example, using a delivery device such as the device illustrated schematically in FIGS. 3A-B, the ligature device 450 is loaded onto the end effector 106 such that the movable arm member 110 is activatable to maintain the arms 452, 454 in a spaced-apart relation—against the spring force of the spring 456—until the target tissue is seated into the device. At that point, the movable arm member 110 is transitioned toward its closed position, allowing the arms 452, 454 to come into closer relation and into the deployment position of the ligature device 450. The device 450 is then released from the delivery device 100.

III. Ligation Systems

Several embodiments of ligature devices and delivery devices are described above. The ligature devices and delivery devices are suitable for delivery and deployment endoscopically or translumenally, including through the use of flexible endoscopic access and delivery devices. For example, in some embodiments, the ligature devices are delivered and deployed using delivery devices that are advanced through one or more channels of a conventional endoscope. In several other embodiments, the ligature devices are delivered and deployed using the delivery devices described in the preceding section and in Table 1 above.

In several embodiments, the ligature delivery device and ligature are advanced into a patient's body to a target site using an endoscopic or translumenal access system such as those described in the United States patent applications referenced above in Table 1. An example of an endoscopic or translumenal access system 500 is shown in FIG. 45. The endoscopic or translumenal access system 500 illustrated in FIG. 45 includes a control mechanism 502 and a multi-lumen, steerable overtube 504 having several features that are described more fully in U.S. patent application Ser. Nos. 11/750,986 and 12/061,591, which were incorporated by reference above. In certain embodiments, the overtube 504 is provided with a mechanism that is capable of selectively rigidizing a portion or all of the shaft 506 of the overtube.

For example, as shown in FIG. 46, a ligature delivery device 100 extends out of a lumen 510 from the distal end of the overtube 504. An endoscope 520 extends from another lumen 512 of the overtube 504. In this orientation, the system user has the ability to visualize the ligature delivery device 100 as it is in use.

IV. Ligation Methods

The ligature devices, delivery devices, and ligation systems described above are suitable for use in a large number of methods and procedures, many of which are described or referenced above. The ligature devices are suitable for delivery and deployment endoscopically, including through the use of flexible endoscopic access and delivery devices. For example, in some embodiments, the ligature devices are delivered and deployed using delivery devices that are advanced through one or more channels of a conventional endoscope. In several other embodiments, the ligature devices are delivered and deployed using the delivery devices described in the preceding section and in Table 1 above.

In several embodiments, the ligature delivery device and ligature are advanced into a patient's body to a target site using an endoscopic or translumenal access system such as those described in the United States patent applications referenced above in Table 1. An example of an endoscopic or translumenal access system is shown in FIG. 45. As discussed above, the endoscopic or translumenal access system illustrated in FIG. 45 includes a control mechanism and a multilumen, steerable overtube having several features that are described more fully in U.S. patent application Ser. Nos. 11/750,986 and 12/061,591, which were incorporated by reference above.

For example, the ligation systems described herein are adapted for use in engaging, grasping, manipulating, and ligating tissue during open surgery, laparoscopic surgery, endoscopic surgery, or translumenal surgery. In particular, the ligation devices and systems are adapted to engage, manipulate, and ligate tissue (e.g., organs, vessels, or other tissue) located within or accessible from the gastrointestinal tract. Alternatively, the devices and systems may be used to engage other human or animal tissue, blood vessels, peritoneal organs, external body surfaces, or tissue of the lung, heart, kidney, bladder, or other body tissue. The devices and systems are particularly useful for engaging, manipulating, and ligating tissue that is difficult to engage using conventional clip applying devices, which frequently occurs during translumenal surgical procedures (e.g., natural orifice translumenal endoscopic surgery, or "NOTES"). Several translumenal procedures are described in U.S. patent application Ser. No. 10/841,233, Ser. No. 10/898,683, Ser. No. 11/238,279, Ser. No. 11/102,571, Ser. No. 11/342,288, and Ser. No. 11/270,195, which are hereby incorporated by reference. The devices and systems described herein are suitable for use in combination with, for example, the endolumenal tool deployment systems described in U.S. patent application Ser. No. 10/797,485, which is hereby incorporated by reference. In particular, the tool deployment systems described in the '485 application includes one or more lumens suitable for facilitating deployment of the medical instruments described herein to perform or assist in performing endoscopic, laparoscopic, or NOTES diagnostic or therapeutic procedures.

Although various illustrative embodiments are described above, it will be evident to one skilled in the art that various changes and modifications are within the scope of the invention. It is intended in the appended claims to cover all such changes and modifications that fall within the true spirit and scope of the invention.

What is claimed is:

1. A method for ligating tissue, comprising:
   providing a device having an elongated flexible shaft and a reverse grasping end effector including a first arm movable relative to a second arm located at or near a distal end of the shaft;
   advancing the end effector into the body of a patient to a location of a target tissue;
   advancing at least the first arm to a position distal of the target tissue in relation to the flexible shaft;
   pivoting the first arm in a first direction by moving an actuator associated with the elongated flexible shaft, such that the end effector forms a tissue engaging shape;
   retracting the end effector to engage the target tissue with the tissue engaging shape;
   pivoting the first arm further in the first direction to compress the target tissue between the first and second arms, and to deform a ligature positioned between the first and second arms around the target tissue; and
   removing the device including the elongated flexible shaft and the reverse grasping end effector from the patient, while leaving the ligature on the target tissue.

2. The method of claim 1, wherein the actuator is within a lumen of the elongated flexible shaft.

3. The method of claim 1, wherein the ligature comprises a deformable clip having a first leg on the first arm and a second leg on the second arm.

4. The method of claim 3 further comprising placing a locking ring onto the clip.

5. The method of claim 1, wherein the end effector is advanced into the body of the patient translumenally.

6. The method of claim 5, wherein the end effector is advanced into the body of the patient through a natural body orifice.

7. The method of claim 1, wherein the first arm member is pivotable more than 90 degrees relative to the second arm member.

8. The method of claim 1, wherein the first arm member is pivotable more than 120 degrees relative to the second arm member.

9. The method of claim 1, wherein the first arm member is pivotable at least 180 degrees relative to the second arm member.

10. The method of claim 1, wherein said device further includes a longitudinal channel defined by said flexible shaft, and a second ligature disposed in the longitudinal channel.

11. The method of claim 10, further comprising deploying said second ligature onto a second target tissue.

12. The method of claim 1, wherein advancing the end effector into the body of a patient further comprises advancing the end effector through a lumen of an overtube having a plurality of lumens extending therethrough such that the flexible shaft is translatably disposed in a first one of said lumens of said overtube.

13. The method of claim 12, further comprising advancing an endoscope through a second one of said lumens of said overtube.

14. The method of claim 13, wherein a distal end of said movable arm is within the field of view of said endoscope.

15. A method for ligating tissue, comprising:
   advancing a reverse grasping end effector on the end of an elongated flexible shaft into the body of a patient to a location of target tissue;
   advancing a first arm of the end effector to a position past the target;
   pivoting the first arm in a first direction to form an acute angle with a second arm on the end effector by pushing or pulling on an actuator linked to at least one of the first and second arms;
   retracting the end effector to engage the target tissue with the acute angle between the first and second arms;
   pivoting the first arm further in the first direction to simultaneously compress the target tissue and to clamp a ligature onto the target tissue;
   pivoting the first arm in a second direction to release the target tissue, with the ligature remaining clamped onto the target tissue; and
   removing the reverse grasping end effector from the location.

16. The method of claim 15 with the ligature comprising a clip having first and second clip arms, and with the pivoting of the first arm bending the first and second clip arms onto the target tissue.

* * * * *